United States Patent
Dablainville et al.

[11] Patent Number: 5,149,502
[45] Date of Patent: Sep. 22, 1992

[54] COLORIMETRIC APPARATUS FOR CONTINUOUS CONTROL OF IMPURITIES ON HYDRATE OF ALUMINA

[75] Inventors: Raymond Dablainville, Gardanne; Jean Dufour, La Barque, both of France

[73] Assignee: Aluminium Pechiney, Courbevoie, France

[21] Appl. No.: 650,790

[22] Filed: Feb. 5, 1991

[30] Foreign Application Priority Data

Feb. 26, 1990 [FR] France .................. 90 02600

[51] Int. Cl.$^5$ .............................. G01N 21/00
[52] U.S. Cl. ........................ 422/62; 422/68.1; 422/82.05; 436/52; 436/55; 436/100; 436/131; 436/164; 198/636; 198/633; 198/810
[58] Field of Search ............ 422/68.01, 62, 82.05, 422/268, 286; 436/55, 131, 100, 52, 164; 198/636, 633, 810, 502.2

[56] References Cited

U.S. PATENT DOCUMENTS

| | | | |
|---|---|---|---|
| 3,856,474 | 12/1974 | Pittman et al. | 422/268 X |
| 3,992,109 | 11/1976 | Bock | 436/164 X |
| 4,010,857 | 3/1977 | Reim et al. | 198/502.2 X |
| 4,029,197 | 6/1977 | Clarke et al. | 198/633 X |
| 4,279,338 | 7/1981 | Sekora | 198/633 X |
| 4,562,059 | 12/1985 | Asaoka et al. | |

FOREIGN PATENT DOCUMENTS

3601932 10/1986 Fed. Rep. of Germany.
2004371 3/1979 United Kingdom.

OTHER PUBLICATIONS

Patent Abstracts of Japan, vol. 13, No. 511 (P-961) (3859) Nov. 16, 1989.

Primary Examiner—James C. Housel
Assistant Examiner—Maureen M. Wallenhorst
Attorney, Agent, or Firm—Dennison, Meserole, Pollack & Scheiner

[57] ABSTRACT

An apparatus for automatic, quantitiative determination of an impurity contained in a product with an uneven upper surface travelling in bulk on a conveyor belt. The apparatus includes a leveling system including a half-cylinder formed of a plastic sheet, and having an arcuate surface downwardly directed toward the belt with the cylinder axis perpendicular to the direction of the belt and having a length which is less than the width of the belt. The half-cylinder is fixed to a frame attached to a lever arm which is in equilibrium about a horizontal shaft. A jack is provided for adjusting the lever arm and enabling the arcuate surface of the half-cylinder to be brought into contact with product travelling on the belt, the jack having a head connected to the lever arm so as to enable the lever arm to oscillate as the leveling device follows variations of the thickness of product travelling on the belt. The apparatus also includes a system for spraying a liquid reagent onto levelled product, a system for measuring the color intensity of the levelled product sprayed by the reagent, a program system for controlling, at predetermined intervals, the adjusting of the lever arm, the spraying of the reagent and the measuring of the color intensity, and a system for determining the quantity of impurity in the product based upon the measured color intensity.

4 Claims, 4 Drawing Sheets

COLORIMETRIC APPARATUS FOR CONTINUOUS CONTROL OF IMPURITIES ON HYDRATE OF ALUMINA

BACKGROUND OF THE INVENTION

The invention comprises a method and apparatus for continuously controlling the caustic soda content of a cake for trihydrate of alumina, $Al(OH)_3$, travelling on a conveyor belt located at the outlet from a rotary drum filter. More generally, the method and apparatus apply to continuously controlling the content of an impurity which can have a colour reaction with a reagent, in a product travelling on a conveyor belt in the form of irregular lumps.

In the Bayer method of preparing alumina by reacting bauxite with caustic soda (FIG. 1), the aluminate liquor obtained is freed from its insoluble impurities in the caustic soda and passes into a series of reactors known as decomposers (1). In the decomposers part of the aluminate in solution is precipitated in the form of insoluble hydrate of alumina, by seeding with germs of hydrate of alumina. The hydrate of alumina is then filtered through a rotary filter (2). The cake obtained naturally contains a large amount of dissolved caustic soda, particularly in the interstitial liquid of the cake. In order to reduce the quantity of caustic soda the process is carried out in two stages:

the cake of hydrate of alumina is put back into suspension in a tank (3) fitted with an agitator, in the washing water from a filter (4) referred to below, to form an alumina milk.

the suspension thus obtained is filtered through a drum filter (4) under vacuum; the cake formed is washed with hot water in the same filter. The washing liquor is passed through the pipe (5) to the tank (3), where it will be used to put the hydrate of alumina into suspension.

The cake obtained on the drum filter (4) after washing is removed from the filter and drops onto a conveyor belt (6) which takes it to the calcining furnace.

For various reasons the free caustic soda content of the hydrate of alumina leaving the drum (4) and travelling towards the calcining station has to be kept below a certain limit, 300 ppm, and it is not essential to go below 175 ppm. The free caustic soda can be determined very easily by acidimetry on samples which are taken from the conveyor belt (6) from time to time. But this is quite a long process: the sample has to be dried in an oven for 3 hours, then extracted with boiling distilled water for 30 minutes, and titrated in the presence of a coloured indicator or a pH meter. Now the throughput of alumina on the conveyor belt is several tens of tonnes per hour; from the time when the sample is taken to the time when the result is obtained, a considerable tonnage of possibly non-standard alumina may be conveyed to the calcining station. In order to avoid too much variation in the product, a worker equipped with a pipette of a phenolphthalein solution is posted near the conveyor belt. By projecting the solution onto the alumina travelling in front of him on the belt, he can ensure—very roughly of course and by estimating the shade of red obtained—that there is no serious variation in the caustic soda content of the product.

SUMMARY OF THE INVENTION

The object of the invention is to convert this rough, discontinuous detection process to a reliable process which does not involve human judgement and which, if not continuous, is at least carried out automatically at adjustable intervals. The project was difficult for several reasons:

Firstly, the throughput of the product on the belt is very irregular; the alumina cake in fact comes away from the drum of the filter in slabs of irregular and uncertain volume. The mean thickness of the product on the belt consequently ranges from 2 to 30 cm with periods of fairly wide variations. This leads to variation in the distance between the top surface of the product and a sensor measuring the colour intensity.

Secondly, in a zone where the mean thickness is relatively constant, the top surface of the product is far from being uniform and parallel with the conveyor belt: the product is in the form of lumps of variable size and shape.

Finally, the colour intensity, which can be used to calculate the caustic soda content, may vary according to the compactness of the product; this influences the diffusion of colouring agent in the measuring zone.

The method described below and the apparatus shown in FIG. 2 show how the above problems have been resolved.

The invention is a combination of three essential means:

the first means is a mechanical system designed to level the top surface of the product travelling on the belt, so that it presents a substantially flat surface at least in the zone where the colorimetry will be carried out.

the second means is a spraying system designed to project the coloured reagent, here a phenolphthalein solution, onto a portion of that top surface.

the third means is a colorimetric determination system which enables the caustic soda content of the alumina to be determined, either by measuring the colour intensity absolutely or by comparing it with a reference colour.

DESCRIPTION OF THE PREFERRED EMBODIMENTS

Figure 2:
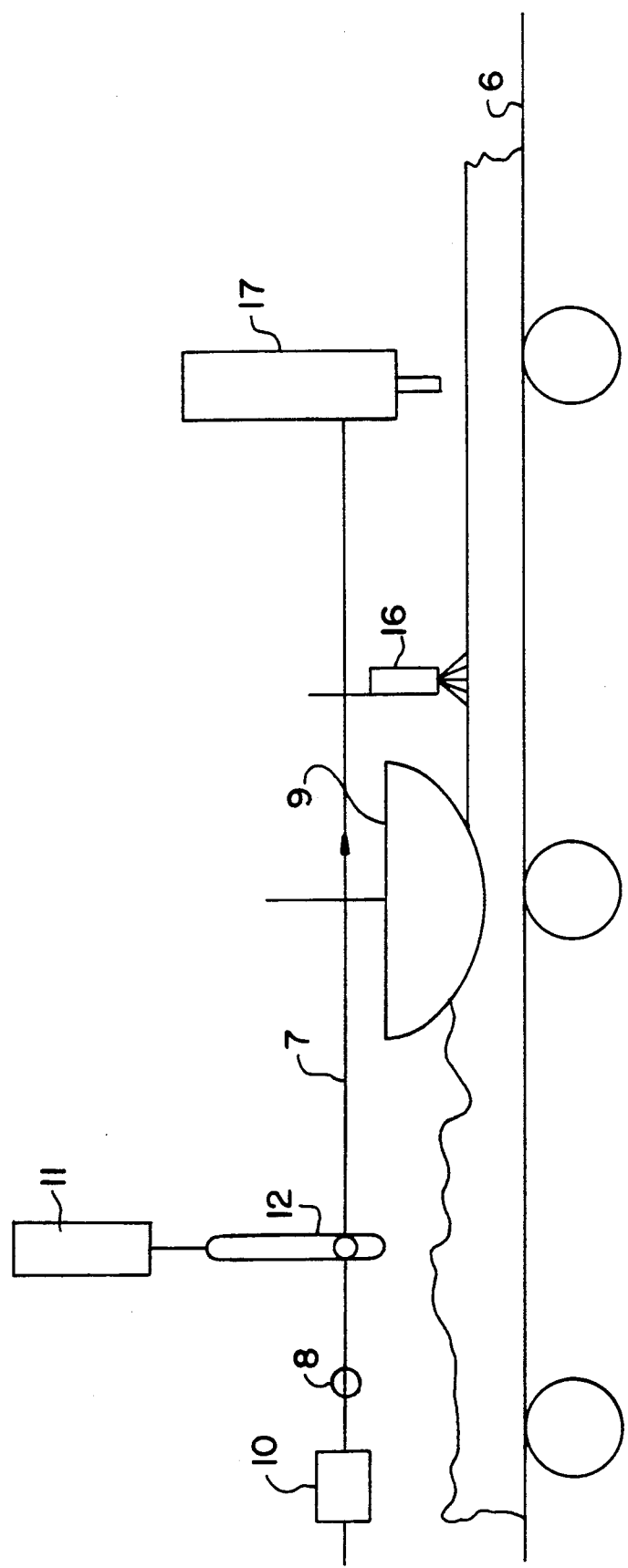
FIG. 2 is a schematic diagram of a process and apparatus according to the invention for levelling and measuring the impurity content in hydrate of alumina travelling on a conveyor belt.

The first means of the invention, as shown in FIG. 2, comprises a lever arm (7) in equilibrium about a horizontal shaft (8) and subjected to several forces: the weight of the levelling arrangement (9), possibly that of the colour measuring system (17) and the weight of a balancing counterweight (10). A jack (11) enables the lever arm (7) to be lowered to bring the levelling arrangement (9) into contact with the product travelling on the belt when a measurement is to be made (it will be seen later that measuring is carried out not continuously but at regular intervals). The head of the jack is not fixed rigidly on the lever arm: it is fixed by means of a substantially vertical slot (12) which allows the lever 7 to oscillate so that the levelling arrangement (9) can follow the variations in thickness of the alumina on the belt.

Figure 3:
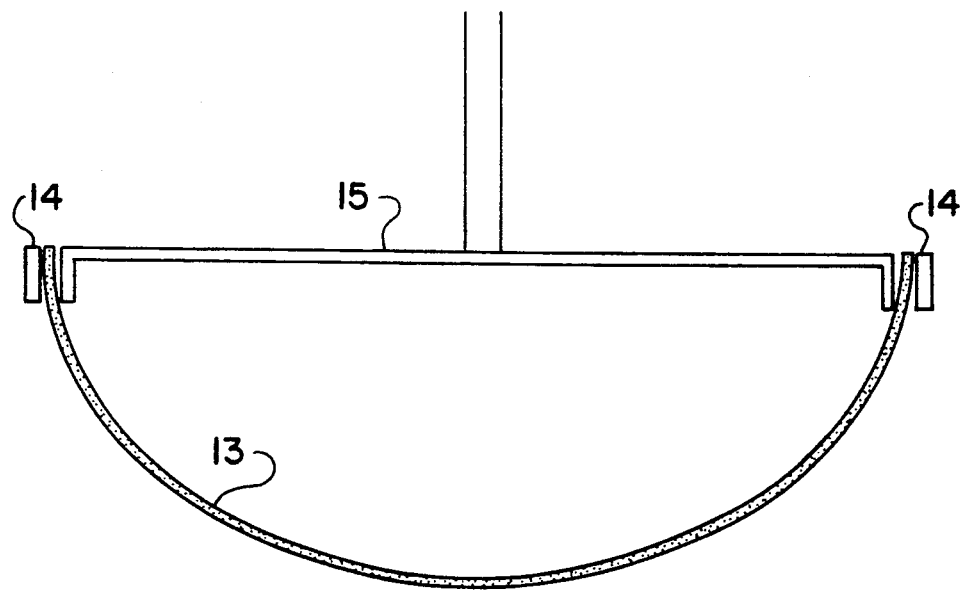
FIG. 3 shows in cross-section a levelling device according to the invention.

The levelling device (9) is shown in FIG. 3; it is a half cylinder (13) made of plastics, which is held at each of its boundary generatrices by two small bars (14) fixed on a frame (15). The half cylinder must have specific properties:

it must be rigid enough to crush the lumps on the surface and give a substantially flat top surface.

yet it must be flexible and deformable enough to let through the lumps which it has not been able to break up.

Applicants have found that a sheet of plastics of the polytetrafluoroethylene type a few millimetres thick is perfectly suitable for this purpose.

The levelling system (9) oscillates about its shaft (8) so as to follow the variations in thickness of the bed of alumina. The bearing force and hence the depth to which the bed of alumina is crushed are controlled by displacing the counterweight (10). The length of the half cylinder obviously need not be equal to the width of the conveyor belt. It is sufficient for it to be slightly larger than the diameter of the stain of colouring agent created by the spraying system.

The second means of the invention is a conventional system (16) for spraying liquids, by compressed air or any other means. It is located between the levelling system (9) and the colorimetric instrument (17) as shown in the figure.

The third means of the invention, shown diagrammatically at (17) in FIG. 2, may be either an instrument for measuring colour continuously or a colour video camera. Each system has specific advantages:

the colour measuring instrument enables absolute measurements to be taken; in other words, this does not necessitate gradation by measuring white at each metering operation. On the other hand it has to operate at a virtually constant distance from the top surface of the bed of alumina; so it is advantageous to fix it on the lever arm supporting the levelling system, thus keeping it at a constant distance by construction. Furthermore its purchase price is higher than that of a camera.

the colour video camera has enough depth of focus not to have to follow the long-period variations in the thickness of the bed. On the other hand a comparative measurement has to be carried out each time, comparing white (without any coloured reagent added) with the colour.

Each of these instruments is of course fitted with an electronic device for processing the signal, enabling the caustic soda content to be either displayed or adjusted by acting on the discharge of washing water on the filter.

EXAMPLE

Figure 1:
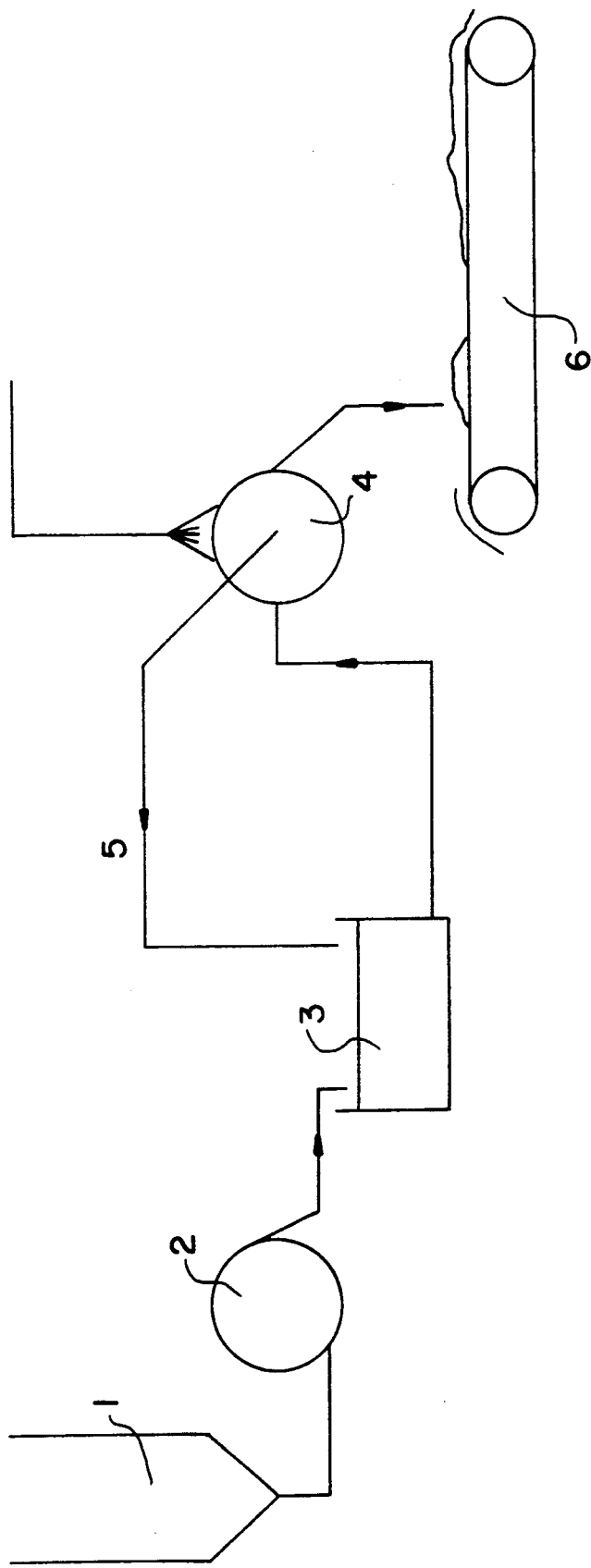
FIG. 1 is a schematic diagram representing a known process and apparatus for obtaining hydrate of alumina.

The measuring system shown in FIG. 2 is installed on the conveyor belt (6) in FIG. 1. The throughput of hydrate of alumina on the belt is approximately 30 tonnes/hour.

The continuous colour measuring system used, an apparatus with the trademark QUAL-PROBE manufactured by Hunterlab, is fixed on the lever arm (7) as shown in FIG. 2.

A programmable controller (not shown) initiates the following operations every 3 minutes:

putting the levelling arrangement (9) into contact with the upper part of the bed of alumina by means of the jack (11).

spraying on a 0.2% by weight solution of phenolphthalein in alcohol for 4 seconds. A pink stain about 6 cm in diameter is obtained.

measuring the color by focussing on a 30 mm diameter section of the surface treated with phenolphthalein.

Samples of hydrate of alumina are taken simultaneously at regular intervals, taking care to note the correspondence between those samples and the colour measurement. In the samples the soluble caustic soda is determined by acidimetry with rosolic acid as the indicator.

Figure 4:
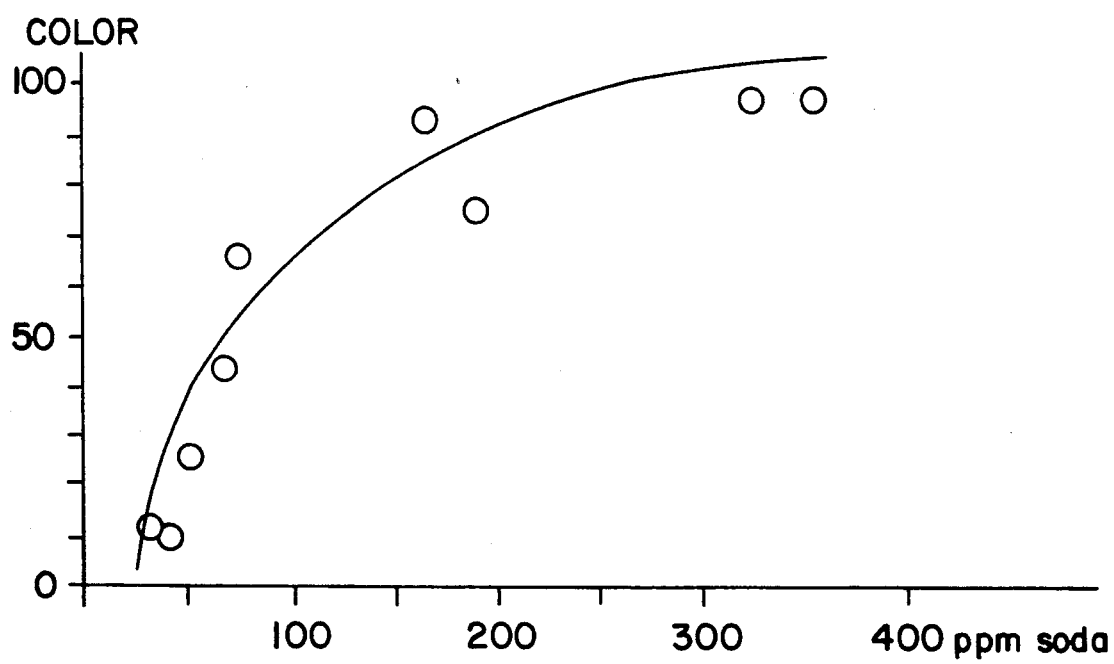
FIG. 4 is a graph of soda content versus color.

FIG. 4 shows the response of the measuring instrument, expressed in arbitrary units, as a function of the quantity of soluble caustic soda determined by acidimetry in the samples, expressed as parts per million of dry hydrate of alumina. The good correlation between these two series of values will be noted; the dispersion of the individual points about the curve has no troublesome effect as far as controlling the industrial process is concerned.

It is clear that the method and apparatus which we have described more particularly for continuously controlling the caustic soda content of hydrate of alumina may be applied, on the principle claimed, to controlling impurities contained in a product travelling in bulk with an uneven top surface, provided the impurities can give a colour reaction with an appropriate reagent.

What is claimed is:

1. Apparatus for automatic, quantitative determination of an impurity contained in a product with an uneven upper surface travelling in bulk on a conveyor belt, the impurity forming a color upon reaction with a known reagent, said apparatus comprising:

(a) a conveyor belt;
   (b) a leveling system comprising:

a leveling device (9) comprising a half-cylinder having a downwardly-directed arcuate surface formed of a plastic sheet (13) located above the conveyor belt, the half-cylinder having a longitudinal axis substantially perpendicular to the direction of travel of the belt and a length which is less than the transverse width of the belt, the plastic sheet being fixed at its boundary generatrices onto a frame (15);

a lever arm (7) above the belt to which said frame is rigidly fixed, said lever arm being supported in equilibrium about a horizontal shaft (8);

a jack (11) for adjusting the lever arm and enabling the arcuate surface of the half-cylinder to be brought into contact with product travelling on the belt, the jack having a head connected to the lever arm, so as to enable the lever arm to oscillate independently of the head as the leveling device follows variations of the thickness of product travelling on the belt;

(c) means (16) for spraying liquid reagent onto leveled product travelling on the belt downstream of the leveling system;
   (d) means (17) for measuring the color intensity of leveled product travelling on the belt downstream of said means (16) for spraying;
   (e) program means for controlling, at predetermined intervals, the jack for adjusting each of the lever arm to selectively bring said half-cylinder into contact with the product on said conveyor belt, the means for spraying of the reagent onto the product, and the means for measuring the color intensity of the product; and (f) means for determining the quantity of said impurity in the product based upon the measured color intensity.

2. The apparatus of claim 1, wherein the means for measuring the color comprises an instrument mounted on said lever arm.

3. The apparatus of claim 2, wherein said lever arm is in said equilibrium by the action of the weight of said levelling device and the weight of said means for measuring the color intensity on one end of said lever arm, and a counterweight (10) on the other end of said lever arm.

4. The apparatus of claim 1, wherein the means for measuring the color intensity comprises a color video camera.

* * * * *